United States Patent [19]
Nelson et al.

[11] Patent Number: 5,451,463
[45] Date of Patent: Sep. 19, 1995

[54] NON-NUCLEOSIDE 1,3-DIOL REAGENTS FOR LABELING SYNTHETIC OLIGONUCLEOTIDES

[75] Inventors: Paul S. Nelson, Union City; Mark A. Kent, Sunnyvale, both of Calif.

[73] Assignee: Clontech Laboratories, Inc., Palo Alto, Calif.

[21] Appl. No.: 71,937

[22] Filed: Jun. 3, 1993

Related U.S. Application Data

[63] Continuation of Ser. No. 800,818, Nov. 29, 1991, abandoned, which is a continuation-in-part of Ser. No. 399,658, Aug. 28, 1989, Pat. No. 5,141,813.

[51] Int. Cl.$^6$ .................. C07C 229/00; C07D 219/00; C07D 311/88; C07F 9/22
[52] U.S. Cl. .................. 428/402; 558/192; 560/155; 568/933
[58] Field of Search .................. 536/25.3, 25.32; 501/33; 560/155; 428/402; 546/25, 102; 548/304.1; 549/223, 227; 552/544; 558/93, 168, 191, 192; 568/933

[56] References Cited

FOREIGN PATENT DOCUMENTS

89/02439  3/1989  WIPO .

OTHER PUBLICATIONS

Nelson et al. Nucl. Acids Res. 17:7179–7186, 1989.
Misiura et al. Nucl. Acids Res. 18:4345–4354, 1990.
Zuckerman, et al. Nucl. Acids Res. 15:5305–5321, 1987.
Smith, L. M., S. Fung, M. W. Hunkapillar, T. K. Hunkapillar, L. E. Hood (1985) "The synthesis of oligonucleotides containing an aliphatic amino group at the 5' terminus: synthesis of fluorescent DNA primers for use in DNA sequence analysis," *Nucl. Acids Res.* 13(7):2399–2412.
Cocuzza, A. J. (1989) "A phosphoramidite reagent for automated solid phase synthesis of 5'-biotinylated oligonucleotides," *Tetrahedron Letters* 30(46):6287–6290.
Hultman, T., S. Bergh, T. Moks, M. Uhlen (1991) "Bidirectional Solid-Phase Sequencing of In Vitro-Amplified Plasmid DNA," *BioTechniques* 10(1):84–93.
Landgraf, A., B. Reckmann, A. Pingoud (1991) "Quantitative Analysis of Polymerase Chain Reaction (PCR) Products Using Primers Laabeled with Biotin and a Fluorescent Dye," *Analytical Biochemistry* 193:231–235.
Connell, C., S. Fung, C. Heiner, J. Bridgham, V. Chakerian, E. Heron, B. Jones, S. Menchen, W. Mordan, M. Raff, M. Recknor, L. Smith, J. Springer, S. Woo, M. Hunkapillar (1987) "Automated DNA Sequence Analysis," *BioTechniques* 5(4):342–346.
Zimran, A., C. Glass, V. S. Thorpe, E. Beutler (1989) "Analysis of'color PCR' by automatic DNA sequencer," *Nucl. Acids Res.* 17(18):7538.
Kaiser, R. J., S. L. MacKellar, R. S. Vinayak, J. Z. Sanders, R. A. Saavedra, L. E. Hood (1989) "Specific primer-directed DNA sequencing using automated fluorescence detection," *Nucl. Acids Res.* 17(15):6087–6102.

*Primary Examiner*—Douglas W. Robinson
*Assistant Examiner*—Gary L. Kunz
*Attorney, Agent, or Firm*—Saliwanchik & Saliwanchik

[57] ABSTRACT

A trifunctional reagent possessing a primary hydroxyl, a secondary hydroxyl, and a primary amino group. This reagent is useful in solid phase oligonucleotide synthesis for the convenient labeling of the 3'-terminus. The secondary hydroxyl may be an phosphoramidite derivative permitting the attachment to the solid phase support. The reporter molecule may be attached to the trifunctional molecule prior to the completion of the oligonucleotide synthesis or after the oligonucleotide is cleaved from the support. A preferred species of this trifunctional molecule is shown below.

15 Claims, 1 Drawing Sheet

Figure 1

NON-NUCLEOSIDE 1,3-DIOL REAGENTS FOR LABELING SYNTHETIC OLIGONUCLEOTIDES

CROSS-REFERENCE TO A RELATED APPLICATION

This application is a continuation of application Ser. No. 07/800,818, filed Nov. 29, 1991, abandoned, which is a continuation-in-part of application Ser. No. 07/399,658, filed Aug. 28, 1989, now U.S. Pat. No. 5,141,813.

BACKGROUND OF THE INVENTION

Methods to covalently attach labels and reporter molecules to oligonucleotides have provided valuable tools in the field of molecular biology and gene probe diagnostics. Recent technologies in non-isotopic gene probes, DNA sequencing (Connell, C. et al. [1987] Biotechniques 5:342–346; Kaiser, R., S. Mackellar, R. Vinayak, J. Sanders, R. Saavedra, L. Hood [1989] Nucleic Acids Res. 17:6087–6102), electron microscopy (Sproat, B. S., B. Beijer, P. Rider [1987] Nucleic Acids Res. 15:6181–6196), and X-ray crystallography (Sproat et al. [1987] Nucleic Acids Res. 15:4837–4848) have provided impetus for the development and improvement of such methods. New and emerging applications employing the polymerase chain reaction (PCR) (Hultman, T., S. Bergh, T. Moks, M. Uhlen [1991] Biotechniques 10:84–93; Landgraf, A., B. Reckmann, A. Pingoud [1991] Analytical Biochemistry 193:231–235; Zimran, A., C. Glass, V. Thorpe, E. Beutler [1989] Nucleic Acids Res. 17:7538) have further expanded the need for convenient and versatile reagents to chemically modify oligonucleotides.

Current methods to introduce chemical modifications into oligonucleotides employ special non-nucleosidic phosphoramidite reagents during automate oligonucleotide synthesis. The methods are limited to single modifications at only the 5' terminus. The inherent disadvantage of such methods is that the reagents terminate chain elongation at the point they are introduced (5' terminus) and therefore only single modifications can be performed. Chemical modifications that have been introduced in this fashion are primary aliphatic amine (Sinha, N. D., R. M. Cook [1988] Nucleic Acids Res. 16:2659–2669) and thiol (Connolly, B. [1985] Nucleic Acids Res. 13:4485–4502) functionalities. Oligonucleotides functionalized with primary aliphatic amines or thiol groups must be subsequently derivatized with labels such as biotin, fluorescein, and enzymes. Subsequent derivatization requires a second reaction and purification step which minimizes the convenience and practicality of this method. Cocuzza expanded this method to directly incorporate a single biotin label into an oligonucleotide at the 5' terminus (Cocuzza, A. [1989] Tetrahedron Lett. 30:6287–6290).

Recently, Nelson et al. introduced a new type of non-nucleosidic phosphoramidite reagent that utilized a 1,2-ethanediol backbone (Nelson, P., R. Sherman-Gold, R. Leon [1989] Nucleic Acids Res. 17:7179–7186). This reagent allowed primary aliphatic amines to be incorporated multiple times and at any position of the oligonucleotide. The development of this method eliminated the termination of chain elongation during synthesis, an inherent problem of the above method. Employment of the 1,2-ethanediol backbone allowed the phosphoramidite reagent to be incorporated exactly like a normal nucleoside phosphoramidite, at any position and multiple times. Misiura et al. expanded the use of the 1,2-ethanediol backbone derived from a glycerol intermediate, to directly incorporate multiple biotins into oligonucleotides (Misiura, K., I. Durrant, M. Evans, M. Gait [1990] Nucleic Acids Res. 18:4345–4354). The development of the 1,2-ethanediol backbone modification method provided better utility and versatility, especially in the field of gene probe diagnostics where multiple labels yield greater signal detection.

There still remain some serious disadvantages in the use of 1,2-ethanediol phosphoramidite modification reagents. First, when internally incorporated into an oligonucleotide, the internucleotide phosphate distance is constricted and is one carbon atom short of the natural 3-carbon atom internucleotide distance. This directly affects hybridization and annealing properties, resulting in destabilization. Secondly, the spacer arm connected to the 1,2-ethanediol backbone is very short (1–4 atoms) Attachment of labels and reporter molecules to the spacer arm can result in steric hindrance being too close to the oligonucleotide. This is an important factor for antibody binding and signal detection. Lastly, the chemistry to modify spacer arm length and to attach different functional groups and labels to the 1,2-propanediol backbone is limited and difficult. Another procedure by Zuckerman et al. (Zuckerman, R., D. Corey, P. Schulz [1987] Nucl. Acids Res. 5305–5321) incorporates a 3' terminal thiol group via solid phase oligonucleotide synthesis. Although this procedure has some advantages, it requires many synthetic steps and purifications.

The purpose of the present invention is to overcome the disadvantages encountered in the prior art by providing improved non-nucleosidic reagents to directly modify or label oligonucleotides via automated solid phase synthesis. Also provided is a unique, simple, and versatile synthesis strategy for modifying spare arm length and attaching different functional groups and labels when preparing such reagents.

BRIEF SUMMARY OF THE INVENTION

The subject invention concerns reagents for use in oligonucleotide synthesis having the following structures:

(I)

(II)

wherein:

SG=an organic spacer group that separates the X groups from the 2-position carbon on the 1,3-propane diol backbone. The preferred embodiment is —(CH$_2$)$_n$—, wherein n is from 0 to about 15.

R$_1$=DMT, MMT, or any other hydroxyl protecting group stable to oligonucleotide synthesis conditions.

R$_2$ is selected from the group consisting of and salts thereof; wherein $R_5$ and $R_6$ are independently selected from the group consisting of $C_{3-10}$ branched alkyl, $C_{1-12}$ unbranched alkyl, and cyclic hydrocarbons; and Y is any phosphate protecting group. In a preferred embodiment, $R_5=R_6 = CH(CH_3)_2$. $R_2$ can also be controlled pore glass (CPG); alkylamine CPG, wherein alkyl is 1 to 50 carbon atoms and isomeric forms thereof; chemically modified CPG; or a suitable polymer; such polymers are known to those skilled in the art and include, for example, polystyrene and divinylbenze.

$X_1$ and $X_2$ = a functional group such as a primary amine (—NH$_2$) or sulfhydryl (—SH) or hydroxyl (—OH) which can be utilized for attaching a label or other desired molecule.

$R_3$ and $R_4$ = any reporter molecule including but not limited to biotin, acridine, fluorophores, or haptens, stable in oligonucleotide synthesis conditions; or $R_3$ and $R_4$ can be any protectional group for the functional group X.

One embodiment of the invention specifically exemplified herein is Biotin-ON™ Phosphoramidite. The general structure of Biotin-ON™ phosphoramidite in reference to Structure I, above, is as follows:

wherein $R_1$=DMT, $R_2$=phosphoramidite, SG is a 4 carbon chain, $X_1$=NH, and $R_3$=biotin.

Other preferred embodiments are exemplified by the following structures:

Alternatively, if $R_2$ of structure I is CPG or a modified CPG structure, preferred embodiments of the subject invention are exemplified by the structures:

The reagents of the subject invention are useful in oligonucleotide synthesis (both oligodeoxyribonucleotide and oligonucleotide) to chemically modify a synthetic oligonucleotide at any position with any chemical functional group. Reagents wherein $R_2$ is CPG (or a modified CPG) are useful for modifications at the 3' terminus. Reagents wherein $R_2$ is not CPG are useful for modifications at the 5' terminus or at internal locations. Useful functional groups (X) are primary amines, sulfhydryls, disulfides, and any other group typically used for conjugation of reporter molecules.

The reagents of the subject invention are useful to directly label oligonucleotides. Also, the subject invention can be used for attaching a label to a functional group introduced at any position of a synthetic oligonucleotide. This "indirect" labeling of the functional group can be accomplished by using a reagent of the subject invention having a protected functional group. Structures VII and X are examples of reagents having protected functional groups. In those examples, the functional amines are protected by Fmoc moieties. Labels which can be directly incorporated using the procedures and methods of the subject invention include, but are not limited to, reporter molecules such as biotin, haptens, and fluorophores. Molecules such as proteins, enzymes, and antibodies can also be used as "labels" by indirect procedures wherein the protected functional group is modified after incorporation into the oligonucleotide.

The reagents and methods of the subject invention can be used to introduce functional groups and labels at multiple sites of a nucleotide during oligonucleotide synthesis. Such modified and labeled oligonucleotide probes can be used in any application where the said probe hybridizes to complementary sequences of a target polynucleotide. Further, primers made from the reagents of the subject invention can be used in the polymerase chain reaction (PCR) to amplify the target gene segment and then employing the invention for detecting the presence of specific polynucleotide in samples containing the same, biological samples, and, for example, clinical samples such as serum and blood. Still further, the subject invention can be used for the diagnosis of infectious diseases and pathogens, detection of oncogenes, diagnosis of genetic disorders, and detection of point mutations or single base substitutions. The subject invention has utility in the areas of anti-sense molecular biology, electron microscopy, X-ray crystallography, and site-specific cleavage of DNA. Also, another important embodiment of the subject invention involves DNA sequencing using procedures well known to those skilled in the art. The use of biotinylated oligonucleotides in the field of molecular biology is rapidly expanding. New applications such as direct solid phase sequencing (Hultman, T., S. Bergh, T. Moks, M. Uhlen [1991] BioTechniques 10:84–93), chemiluminescent sequencing (Martin, C., L. Bresnick, R. R. Juo, J. C. Voyta, I. Bronstein [1991] BioTechniques 11:110–113), and quantitative analysis (Landgraf, A., B. Reckmann, A. Pingoud [1991] Anal. Biochem. 193:231–235) of PCR products have recently emerged. The reagents of the subject invention can readily be used by those skilled in the art in these emerging technologies.

A preferred embodiment of the subject invention is a novel multifunctional reagent, Biotin-ON TM Phosphoramidite, useful to directly incorporate biotin labels into synthetic oligonucleotides. Biotin-ON TM Phosphoramidite comprises a unique structure which possesses a biotin label attached through a spacer arm and a dimethoxytrityl protected hydroxyl for nucleotide chain elongation. Using Biotin-ON TM Phosphoramidite, it is simple and convenient to attach labels internally or to the 5' terminus of oligonucleotides. Labels can also be added to the 3' terminus using CPG embodiments.

A key feature of the invention is the non-nucleosidic 1,3-diol backbone. This unique feature allows for chain elongation during automated solid phase oligonucleotide synthesis. This 1,3-diol backbone gives the invention the following features:

1. When added to the oligonucleotide the natural internucleotide distance between phosphate groups is conserved. The natural distance is 3 carbons between phosphate groups, and the 1,3-propanediol backbone mimics this natural distance. This is an important property of annealing and hybridization functions. This maintenance of internucleotide phosphate distance is a very unique and important feature.

2. Multiple unit additions of the reagent can be made by repetitive coupling cycles. This is an important feature for detection sensitivity since more labels gives more signal. It also is important for binding or capture properties.

3. The reagent can be inserted (added) at any desired position of the oligonucleotide.

No prior reagent is known to possess all of these advantageous features. All other patents and prior technology do not include the three features mentioned above for non-nucleosidic, acyclic modification reagents. Another unique feature of the invention is:

4. The label and spacer arm (optional) are attached to the 2-position. The novel synthetic route allows for easy construction of the 2-position linking arm and label. The chemistry is very versatile, starting with an addition reaction to the 2-position of diethyl malonate (an inexpensive and readily available chemical). The 2-position spacer arm and label can be subsequently built with routine reactions. Virtually any label, tag, or reporter molecule can be added to the 2-position through any desired linking arm. Various spacer arms and labels which are attached to the 2-position of the 1,3 propanediol backbone are intended to be encompassed by this invention.

As described above, this invention can be applied to the solid phase CPG (controlled pore glass) synthesis. By replacing the phosphoramidite group with a CPG group, direct 3' modification can be achieved. This aspect of the invention retains the 1,3 propanediol backbone with the 2-position modification benefits.

DETAILED DESCRIPTION OF THE INVENTION

Figure 1:
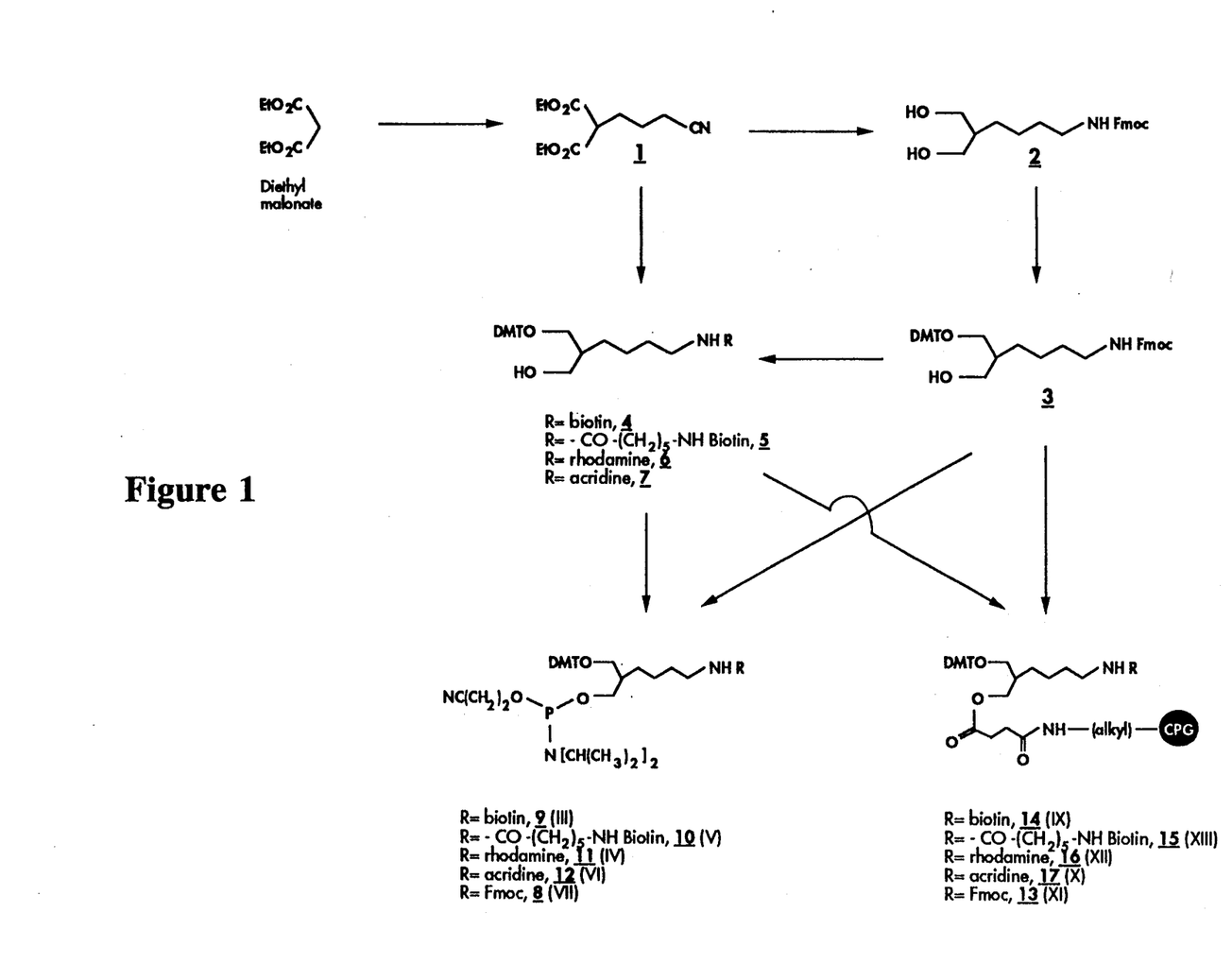
FIG. 1 is a schematic drawing of the various reactions used to produce compounds of the subject invention. Arabic numerals refer to compound numbers given in examples, while Roman numerals refer to structure numbers in the Brief Summary of the Invention.

The reagents of the subject invention are useful in oligonucleotide synthesis (both oligodeoxyribonucleotide and oligonucleotide) to chemically modify a synthetic oligonucleotide at any position with any chemical functional group.

In a preferred embodiment, the reagents and methods of the subject invention enable the biotinylation of oligonucleotides at multiple sites and at any position including internal sites and the 5' terminus. These reagents, which couple exactly like normal CE-phosphoramidites, are designed for use with any automated DNA synthesizer. Advantageously, the reagents are soluble in acetonitrile and are stable to ammonium hydroxide deprotection. A further advantage of the methods and reagents of the subject invention is that it is possible to maintain the natural distance and structure between internucleotide phosphate groups. Furthermore, the reagents of the subject invention may comprise a dimethyoxyltrityl (DMT) group for easy determination of coupling efficiency. With the use of reagents wherein $R_2$ is CPG, or a modification thereof, modifications at the 3' terminus can be achieved.

Therefore, the reagents of the subject invention are specifically constructed for chain elongation and internal insertions. When used for internal insertion, the reagents have been engineered to retain the natural internucleotide phosphate distance. As a result of these reagents' unique construction, they can be incorporated at any position in an oligonucleotide, and they can be incorporated multiple times. We have also constructed a DMT protected hydroxyl group to quantify coupling efficiencies for multiple internal incorporation. Typical coupling efficiencies are greater than 95% as determined by UV measurement of the dimethoxytrityl group. Conventional ammonia hydroxide cleavage and deprotection did not result in any decomposition of the incorporated biotin entity. These differences make the novel reagents both unique in molecular structure and in use. The subject invention can also incorporate controlled pore glass (CPG) in place of the phosphoramidite group for solid phase nucleotide elongation or 3' modification procedures. Preferably, the CPG comprises a unique multifunctional linking arm to give a multifunctional CPG, MF-CPG ®, which transfers a primary amine to the 3' terminus of a synthesized oligonucleotide without changing any chemistry or adding extra steps.

Another important aspect of one embodiment of this invention is a 12-atom spacer arm that connects the biotin moiety to the 2-position of the 1,3-propanediol backbone. We have observed the longer spacer arm to result in better streptavidin binding on magnetic particles. This is an important aspect in direct solid phase sequencing.

Following are examples which illustrate procedures, including the best mode, for practicing the invention. These examples should not be construed as limiting. All percentages are by weight and all solvent mixture proportions are by volume unless otherwise noted.

EXAMPLE 1

Preparation of 2-Butyrylnitrile Diethyl Malonate (Compound 1)

Dissolve 311.9 g (96%, 4.4 mol) NaOEt (MW 68.06) in 1600 ml anhydrous EtOH. Cool flask in ice bath. Add 704 g (4.4 mol) diethylmalonate (MW 160.19) dropwise with thorough stirring. Add 592 g (4.0 mol) 4-bromobutyronitrile (MW 148.01) dropwise with stirring. Bring slowly to reflux, and reflux for 2.5 hours. Partition between water and EtOAc. Wash the organic with 2×1.5 L brine, and dry over anhydrous $Na_2SO_4$. Concentrate by rotary evaporation. Distill under vacuum at 0.5 torr; collect 154°–156° C. fractions. yield: 555.4 g (61.1%).

EXAMPLE 2

Preparation of 2-(N-Fmoc-4-aminobutyryl)-1,3-propanediol (Compound 2)

Dissolve 220.9 g (0.97 mol) 2-butyronitrile diethylmalonate (1) in 1200 ml anhydrous toluene with stirring. Heat solution to gentle reflux. Add 1600 ml (3.2 mol, 3.3× equiv.) $BH_3.Me_2S$ (2M solution in toluene) very slowly using a cannula and Ar pressure. Gently reflux for 45 hours, with thorough stirring. Cool in an ice bath. Add 300 ml MeOH slowly with mechanical stirring, to quench reaction, then 5 ml concentrated HCl, and then another 300 ml MeOH in one portion. Check the pH of the solution at this point: pH should be about 7.5. Add 45 ml concentrated HCl, and stir at ambient temperature for 15 minutes. Check the pH again: pH should be about 2.0. Set up for distillation and distill off toluene and dissolve residue in 750 ml DMF and 450 ml (2.58 mol) anhydrous diisopropylethylamine with thorough stirring. Cool the reaction mixture to 10° C. in an ice bath. Add 243.0 g (0.94 mol, MW 258.70) Fmoc-Cl portionwise with thorough stirring and allow to react for 30 minutes. Evaporate in vacuo to dryness using hard vacuum at 35° C. Partition between 2500 ml EtOAc and 100 ml $H_2O$. Wash 2×100 ml $H_2O$ and 1×100 ml brine. Dry over $Na_2SO_4$. Concentrate by rotary evaporation to about 20% of original volume, then filter through a dry 0.5" Celite pad. Purify on a silica gel column (10 cm diameter), using $CH_2Cl_2$ as elution solvent. Elute with 5 L of $CH_2Cl_2$, 12 L of 2.5% MeOH in $CH_2Cl_2$, 2.5 L of 5% MeOH in $CH_2Cl_2$, and then 4 L of 10% MeOH in $CH_2Cl_2$. Monitor fractions by TLC, using 9:1 $CH_2Cl_2$: MeOH to develop and $H_2SO_4$ followed by heating to scorch and visualize. Pool appropriate fractions and remove solvent in vacuo to get a white solid. Yield: 192 g.

EXAMPLE 3

Preparation of 1-O-DMT-2-(N-Fmoc-4-aminobutyryl)-1,3-propanediol (Compound 3)

Weigh 170 g (0.461 mol) 2-(N-Fmoc-4-aminobutyryl)-1,3-propanediol (2). Dissolve in 900 ml anhydrous pyridine with magnetic stirring. Stir until dissolved. Add portionwise 171.0 g (0.504 mol) DMT-Cl. Stir clear yellow solution 18 hours at room temperature. Concentrate in vacuo. Co-evaporate 2×250 ml toluene. Partition residue between 800 ml EtOAc and 200 ml $H_2O$. Wash 2×400 ml brine. Dry over $Na_2SO_4$. Concentrate in vacuo, co-evaporate using 2×250 ml anhydrous toluene to completely remove pyridine. Load onto a silica gel column (10 cm diameter), using 2.5% EtOAc in $CH_2Cl_2$. Elute product with 2.5% EtOAc in $CH_2Cl_2$ (8 L) then 15% EtOAc in $CH_2Cl_2$ (9 L). Pool appropriate fractions containing product and strip solvent off on rotovap. Yield: 101.0 g (40.8%).

EXAMPLE 4

Preparation of 1-O-DMT-2-(N-Biotin-4-aminobutyryl)1,3-propanediol (Compound 4)

Dissolve 101 g (0.150 mol, MW 671.89) of 1-O-DMT-2-N-Fmoc-4-aminobutyryl)-1,3-propanediol (3) in 100 ml hot isopropyl alcohol with swirling until the bulk of the material has dissolved. Transfer the solution, using the remaining 300 ml of hot isopropyl alcohol. Slowly and carefully add 102 g (2.77 mol, MW 37.83) sodium borohydride in small portions with thorough stirring. Stir at 70° C. for 40 minutes. Check reaction progress by TLC using $MeOH:CH_2Cl_2:NH_4OH$ (10:10:1) to develop and $H_2SO_4$ to visualize. Product $R_f 0.35$; starting material at $R_f 0.8$. Cool reaction mixture in an ice bath to approximately 5° C. and quench by dropwise addition of 800 ml 10% NaOH. Allow mixture to warm to room temperature with stirring. Add to EtOAc and partition the reaction mixture between phases. Wash the organic phase 2×500 ml brine. Dry over $Na_2SO_4$ for 15 minutes and concentrate in vacuo. Dissolve the crude product (98.5 g) in 575 ml dry DMF, and add 52.2 g Biotin-NHS ester and 35 ml anhydrous diisopropylethylamine. Warm slightly to get a complete solution once all of the components are added. Allow to react overnight at room temperature under argon. Remove solvent by rotary evaporation at 50° C. under high vacuum. Partition between 2 L EtOAc and 600 ml water. Wash organic layer with 1×650 ml 10% $Na_2CO_3$ and 1×650 ml brine. Dry over $Na_2SO_4$ and concentrate in vacuo. Take residue up in 300 ml $CH_2Cl_2$; add 200 g silica gel. Mix thoroughly on rotovap. Remove solvent using aspirator then high vacuum until dry (flows freely). Dry pack column (6.5 cm diameter) to 49 cm height with silica gel. Load sample/silica gel mixture onto top of column. Elute product from column with $CH_2Cl_2$ (3 L), then 95:5 $CH_2Cl_2$:MeOH (4 L) and then 9:1 $CH_2Cl_2$:MeOH (8 L). Pool appropriate fractions and concentrate in vacuo. Yield: 89.7 g (86.3%).

EXAMPLE 5

Preparation of 1-O-DMT-2-(N-Biotin-LC-4-Aminobutyryl)-1,3-propanediol (Compound 5)

Dissolve 33.9 g (50.45 mmol) of 1-O-DMT-2-(N-Fmoc-4-aminobutyryl)-1,3-propanediol (3) in 250 ml hot isopropanol with magnetic stirring. Slowly and carefully add 34.2 g (305 mmol, MW 37.83) sodium borohydride in small portions with thorough stirring. Stir at approximately 70° C. for 45 minutes. Cool reaction mixture in an ice bath and carefully add 270 ml 10% NaOH dropwise. Remove ice bath and stir for 15 minutes allowing mixture to warm to room temperature. Add 340 ml ethyl acetate and partition phases. Separate the phases, and wash the organic phase 2×170 ml brine. Dry over $Na_2SO_4$ for 15 minutes and concentrate in vacuo. Dissolve the crude product in 200 ml dry DMF, add 24.1 g Biotin-X-NHS ester and 12 ml anhydrous diisopropylethylamine. Allow to react overnight at room temperature. Check reaction progress with TLC, using $CH_2Cl_2$:MeOH (9:1) to develop TLC plate, and sulfuric acid to visualize. $R_f$ product=0.4. Concentrate by rotary evaporation at 50° C. under high vacuum. Partition between 670 ml EtOAc and 200 ml water. Wash organic layer with 1×220 ml 10% $Na_2CO_3$ and 1×220 ml brine. Dry over $Na_2SO_4$ for 15 minutes and concentrate in vacuo. Take residue up in 100 ml $CH_2Cl_2$; add 67 g silica gel. Mix thoroughly and evaporate to dryness. Dry pack column with silica gel and load sample/silica gel mixture onto top of column. Elute product from column, starting with $CH_2Cl_2$ (3), 95:5 $CH_2Cl_2$:MeOH (4 L), and then 9:1 $CH_2Cl_2$:MeOH (6 L). Pool appropriate fractions and concentrate in vacuo. Yield: 24.8 g (62.3%) of off-white solid.

EXAMPLE 6

Preparation of 2-(N-rhodamine-4-aminobutyryl)-1,3-propanediol (Compound 6)

Dissolve 18.0 g (0.079 mol) 2-butyronitrile diethylmalonate (1) in 80 ml anhydrous toluene with stirring. Heat solution to gentle reflux. Add 131 ml (0.261 mol, 3.3× equiv.) $BH_3.Me_2S$ (2M solution in toluene) very slowly using a cannula and Ar pressure. Gently reflux for 46 hours, with thorough stirring. Cool in an ice bath. Add 50 ml MeOH slowly with mechanical stirring, to quench reaction. Add HCl to litmus pH of 2.0. Evaporate to a gummy residue in vacuo. Dissolve in 65 mM of DMF and add 39.5 g (0.079) rhodamine isothiocyanate. React for 4 hours at room temperature and concentrate in vacuo. Partition between 150 ml EtOAc and 50 ml water. Wash 2×50 ml water, 1×50 ml brine, and dry over $Na_2SO_4$. Concentrate in vacuo and load on silica gel column (5 cm diameter). Elute with stepwise gradient of $CH_2Cl_2$, 2.5% MeOH in $CH_2CL_2$, 5% MeOH in $CH_2CL_2$, and 10% MeOH in $CH_2CL_2$. Pool appropriate fraction and concentrate in vacuo to dryness. Yield: approximately 35 g.

EXAMPLE 7

Preparation of 2-(N-acridine-4-aminobutyryl)-1,3-propanediol (Compound 7)

Dissolve 18.0 g (0.079 mol) 2-butyronitrile diethylmalonate (1) in 80 ml anhydrous toluene with stirring. Heat solution to gentle reflux. Add 131 ml (0.261 mol, 3.3× equiv.) $BH_3.Me_2S$ (2M solution in toluene) very slowly using a cannula and Ar pressure. Gently reflux for 46 hours, with thorough stirring. Cool in an ice bath. Add 50 ml MeOH slowly with mechanical stirring, to quench reaction. Add HCl to litmus pH of 2.0. Evaporate to a gummy residue in vacuo. Dissolve in 65 mM warm phenol and 29 ml (0.166 mol) diisopropylethylamine. Add 22 g (0.073 mol) of 6,9-dichloro-2-methoxyacridine. React at 110° C. for 1 hour. Cool reaction mixture and add 35 ml methanol. Pour mixture into 475 ml of cold 10% sodium hydroxide. The resulting yellow precipitate was collected by filtration and washed with 1N sodium hydroxide (4×100 ml). The precipitate was taken up in 300 ml refluxing methanol. The undissolved solid was removed by filtration and the filtrate was evaporated in vacuo to a yellow orange solid (16.7 g).

EXAMPLE 8

Preparation of Uni-Link TM AminoModifier (Compound 8/Structure VII)

Dissolve 33.9 g (0.050 mol) 1-O-DMT-2-(N-Fmoc-4-aminobutyryl)-1,3-propanediol (3) in 17 ml (0.089 mol) diisopropylethylamine and 225 ml anhydrous $CH_2Cl_2$ with stirring under Ar. Add 11.2 g (0.048 mol) chloro-N,N-diisopropyl-beta-cyanoethylphosphoramidite slowly, and stir at room temperature for 30 minutes. Add 1.8 ml MeOH through the septum to quench the phosphitylating reagent and stir an additional 10 minutes. Take sample up in 800 ml base-washed EtOAc. Wash the organic layer with 800 ml 10% $Na_2CO_3$, then with 800 ml brine. Dry over $Na_2SO_4$. Take TLC of sample, using 60:30:10 hexanes:EtOAc:$Et_3N$ to develop sample; visualize with $H_2SO_4$ scorch. The product is at $R_f$=0.47. Remove solvent using rotary evaporation in vacuo. Load sample onto a silica gel column. Elute with a step gradient of hexanes:$CH_2Cl_2$:$Et_3N$, 55:35:3 hexanes:$CH_2Cl_2$:$Et_3N$ (2 L), and 55:45:3 hexanes:$CH_2Cl_2$:$Et_3N$ (4 L). Pool appropriate fractions and strip off solvents on rotovap. Co-evaporate with 200 ml benzene to remove $Et_3N$. Immediately dry sample under high vacuum at room temperature overnight. Yield: 30.5 g (70%).

EXAMPLE 9

Preparation of Biotin-ON TM Phosphoramidite (Compound 9/Structure III)

Weight 10.0 g (0.0148 mol, MW 675.96) 1-O-DMT-2-((N-Biotin)-4- aminobutyryl)-1,3-propanediol (4) into a clean dry 250 ml RB flask. Dissolve starting material in 55 ml of anhydrous dichloromethane with magnetic stirring. Add 1.1 g tetrazole (15.7 mmol) with thorough stirring for 15 minutes. Add 5.7 ml (1 mmol, MW 301.5, 1.2× excess) phosphitylating reagent dropwise into the reaction mixture with thorough stirring and allow to react for 15 minutes. Load directly onto a silica gel column packed in 8:2:1 $CH_2Cl_2:CH_3CN:Et_3N$. Elute product isocratically with same solvent. Pool appropriate fractions and immediately concentrate by rotary evaporation. Place under high vacuum at room temperature overnight. Yield: 6.5 g (51%).

EXAMPLE 10

Preparation of LC-Biotin-ON ™ Phosphoramidite (Compound 10/Structure V)

Dissolve 11.68 g (0.0148 mol, MW 789.16) 1-O-DMT-2-(N-Biotin-LC-4-aminobutyryl)-1,3-propanediol (5) in 150 ml of anhydrous dichloromethane with magnetic stirring. Add 1.1 g tetrazole (15.7 mmol) and stir for exactly 15 minutes. Draw 5.5 ml (17.3 mmol, d 0.95, 1.2× excess) of 2-cyanoethyl-N,N,N'-N'-tetraisopropyl phosphoramidite into a graduated pipet and add dropwise into the reaction mixture with thorough stirring. React for 15 minutes at room temperature. Load directly onto silica gel column. Elute product isocratically with 7:2:1 $CH_2Cl_2:CH_3CN:Et_3N$. Product should appear after about 1.5 liters of eluent. Pool appropriate fractions and remove solvent in vacuo. Place under high vacuum at room temperature overnight. Yield: 6.5 g (51%).

EXAMPLE 11

Preparation of Rhodamine-ON ™ Phosphoramidite (Compound 11/Structure IV).

Dissolve 14.1 g (0.0148 mol) 1-O-DMT-2-(N-Rhodamine-4-aminobutyryl)-1,3-propanediol (6) in 150 ml of anhydrous dichloromethane with magnetic stirring. Add 1.1 g tetrazole (15.7 mmol) and stir for exactly 15 minutes. Draw 5.5 ml (17.3 mmol, d 0.95, 1.2× excess) of 2-cyanoethyl-N,N,N'-N'-tetraisopropyl phosphoramidite into a graduated pipet and add dropwise into the reaction mixture with thorough stirring. React for 15 minutes at room temperature. Load directly onto silica gel column. Elute product isocratically with 7:2:1 $CH_2Cl_2:CH_3CN:Et_3N$. Product should appear after about 1.5 liters of eluent. Pool appropriate fractions and remove solvent in vacuo. Place under high vacuum at room temperature overnight. Yield: 8.0 g.

EXAMPLE 12

Preparation of Acridine-ON ™ Phosphoramidite (Compound 12/Structure VI)

Dissolve 10.0 g (0.0149 mol) 1-O-DMT-2-(N-acridine-4-aminobutyryl)-1,3-propanediol (7) in 150 ml of anhydrous dichloromethane with magnetic stirring. Add 1.1 g tetrazole (15.7 mmol) and stir for exactly 15 minutes. Draw 5.5 ml (17.3 mmol, d 0.95, 1.2× excess) of 2-cyanoethyl-N,N,N'-N'-tetraisopropyl phosphoramidite into a graduated pipet and add dropwise into the reaction mixture with thorough stirring. React for 15 minutes at room temperature. Load directly onto silica gel column. Elute product isocratically with 7:2:1 $CH_2Cl_2:CH_3CN:Et_3N$. Product should appear after about 1.5 liters of eluent. Pool appropriate fractions and remove solvent in vacuo. Place under high vacuum at room temperature overnight. Yield: 6.0 g.

EXAMPLE 13

Preparation of DMT-C6-3'Amine-ON ™ CPG (Compound 13/Structure XI)

Dissolve 38.3 g (0.057 mol) 1-O-DMT-2-((N-Fmoc)-4-aminobutyryl)-1.3-propanediol (3) in 160 ml anhydrous pyridine with stirring. Add 3.2 g (0.026 mol) p-dimethylaminopyridine (DMAP, MW 122,19) and 4.75 g (0.048 mol) succinic anhydride (MW 100). Stir reaction mixture at room temperature for 24 hours. Take a TLC to check whether reaction is completed. Develop with 9:1 $CH_2Cl_2$:MeOH, with 2 drops of $NH_4OH$ in the TLC development chamber. Scorch with $H_2SO_4$ to visualize. The product spot will be at $R_f=0.32$; unreacted starting material will be at the solvent front. Strip solvent off on rotovap, using high vacuum. Transfer oil into a 2 L separatory funnel containing 1400 ml EtOAc. Wash 3×700 ml brine and dry over anhydrous $Na_2SO_4$. Remove solvent by rotary evaporation in vacuo. Co-evaporate 2×150 ml anhydrous pyridine. Immediately add 225 ml anhydrous dioxane, 7.5 ml anhydrous pyridine, and 11.8 g (0.085 mol) p-nitrophenol to flask with magnetic stirring. Cool reaction flask to 25° C. and add 16.0 g (0.078 mol) dicyclohexylcarbodiimide with stirring, and stir at room temperature for 4 hours. Add 8 ml $Et_3N$ to the reaction mixture and swirl to mix. Filter reaction mixture through a sintered glass funnel directly into a flask of 100 g long chain alkylamine CPG. Add more anhydrous dioxane, if necessary, in order to get a proper consistency. Shake 48 hours. Collect the derivatized CPG by filtration in a clean 2 L sintered glass funnel. Wash with 3×1000 ml DMF, 3×100 ml MeOH, and 3×1000 ml ether. Transfer the CPG to a clean, dry 2 L RB flask and dry by rotary evaporation, using aspirator, then pump at hard vacuum for an hour to remove all solvents. Cap unreacted amines by treating CPG with 70 ml acetic anhydride, 280 ml anhydrous pyridine, and 1.3 g DMAP. Swirl on orbital shaker for 2 hours. Collect the capped CPG by filtration in a 2 L sintered glass funnel. Wash with 1×1500 ml pyridine, 3×1000 ml DMF, 2×1000 ml water, 3×1000 ml MeOH, and 3×1000 ml ether. Dry in vacuo. Yield: 100 g.

EXAMPLE 14

Preparation of Biotin-ON ™ CPG (Compound 14/Structure IX)

Dissolve 1-O-DMT-2-((N-Biotin)-4-aminobutyryl)-1,3-propanediol (4) (7.0 g, 10.4 mmol) in 30 ml anhydrous pyridine with stirring. Stir at room temperature. Add p-dimethylamino-pyridine (0.584 g, 4.8 mmol) and succinic anhydride (0.863 g, 8.63 mmol). Stir reaction mixture at room temperature for 24 hours. Analyze by TLC to check whether reaction is completed, using 1:1 MeOH:$CH_2Cl_2$ with 4 drops of $NH_4OH$ added to develop; visualize with $H_2SO_4$ ($R_f$product=0.5). Remove solvent by rotary evaporation using high vacuum. Partition between 250 ml EtOAc and 100 ml $H_2O$. Wash 3×130 ml brine. Combine aqueous layers and extract with 300 ml EtOAc. Dry the organics over anhydrous $Na_2SO_4$. Remove solvent by rotary evaporation in vacuo. Co-evaporate 2×50 ml anhydrous pyridine. Immediately add 41 ml anhydrous dioxane. Swirl flask to achieve complete solution. Add 7.5 ml anhydrous pyridine and p-nitrophenol (2.15 g, 15.5 mmol) to flask with magnetic stirring. Cool reaction flask to 25° C. Add dicyclohexylcarbodiimide (2.92 g, 14.3 mmol, MW 204.35) with stirring, and stir at room temperature for 4 hours. Add 1.6 ml triethylamine and stir 10 minutes. Filter reaction mixture through a sintered glass funnel directly into 18 g long chain alkylamine CPG. Agitate the CPG mixture for 24 hours. Collect the derivatized CPG by filtration into a clean 600 ml sintered glass funnel. Wash with $3\times 500$ ml DMF, $3\times 500$ ml MeOH, and $3\times 500$ ml ether. Transfer the CPG to a clean, dry 500 ml RB flask and dry on the rotovap, using aspirator, then pump at hard vacuum for an hour to remove all solvents. Mix together 12.7 ml acetic anhydride, 51 ml anhydrous pyridine, and 236 mg DMAP. Cap the CPG by adding this solution to the dry CPG and swirl on orbital shaker for 2 hours. Collect the capped CPG by filtration in a clean 500 ml sintered glass funnel. Wash with $1\times 1000$ ml pyridine, $3\times 500$ ml DMF, $2\times 500$ ml water, $3\times 500$ ml MeOH, and $3\times 500$ ml ether. Dry in vacuo.

EXAMPLE 15

Preparation of LC Biotin-ON™ CPG (Compound 15/Structure XIII)

Dissolve 1-O-DMT-2-(N-Biotin-LC-4-aminobutyryl)-1,3-propanediol (8.2 g, 10.4 mmol) (5) in 30 ml anhydrous pyridine with stirring. Stir at room temperature. Add p-dimethylamino-pyridine (0.584 g, 4.8 mmol) and succinic anhydride (0.863 g, 8.63 mmol). Stir reaction mixture at room temperature for 24 hours. Analyze by TLC to check whether reaction is completed, using 1:1 MeOH:CH$_2$Cl$_2$ with 4 drops of NH$_4$OH added to develop; visualize with H$_2$SO$_4$ ($R_f$ product=0.5). Remove solvent by rotary evaporation using high vacuum. Partition between 250 ml EtOAc and 100 ml H$_2$O. Wash $3\times 130$ ml brine. Combine aqueous layers and extract with 300 ml EtOAc. Dry the organics over anhydrous Na$_2$SO$_4$. Remove solvent by rotary evaporation in vacuo. Co-evaporate $2\times 50$ ml anhydrous pyridine. Immediately add 41 ml anhydrous dioxane. Swirl flask to achieve complete solution. Add 7.5 ml anhydrous pyridine and p-nitrophenol (2.15 g, 15.5 mmol) to flask with magnetic stirring. Cool reaction flask to 25° C. Add dicyclohexylcarbodiimide (2.92 g, 14.3 mmol, MW 204.35) with stirring, and stir at room temperature for 4 hours. Add 1.6 ml triethylamine and stir 10 minutes. Filter reaction mixture through a sintered glass funnel directly into 18 g long chain alkylamine CPG. Agitate the CPG mixture for 24 hours. Collect the derivatized CPG by filtration into a clean 600 ml sintered glass funnel. Wash with $3\times 500$ ml DMF, $3\times 500$ ml MeOH, and $3\times 500$ ml ether. Transfer the CPG to a clean, dry 500 ml RB flask and dry on the rotovap, using aspirator, then pump at hard vacuum for an hour to remove all solvents. Mix together 12.7 ml acetic anhydride, 51 ml anhydrous pyridine, and 236 mg DMAP. Cap the CPG by adding this solution to the dry CPG and swirl on orbital shaker for 2 hours. Collect the capped CPG by filtration in a clean 500 ml sintered glass funnel. Wash with $1\times 1000$ ml pyridine, $3\times 500$ ml DMF, $2\times 500$ ml water, $3\times 500$ ml MeOH, and $3\times 500$ ml ether. Dry in vacuo. Yield: 18 g.

EXAMPLE 16

Preparation of Rhodamine-ON™ CPG (Compound 16/Structure XII)

Dissolve 1-O-DMT-2-(N-rhodamine-4-aminobutyryl)-1,3-propanediol (9.9 g, 10.4 mmol) (6) in 30 ml anhydrous pyridine with stirring. Stir at room temperature. Add p-dimethylamino-pyridine (0.584 g, 4.8 mmol) and succinic anhydride (0.863 g, 8.63 mmol). Stir reaction mixture at room temperature for 24 hours. Analyze by TLC to check whether reaction is completed, using 1:1 MeOH:CH$_2$Cl$_2$ with 4 drops of NH$_4$OH added to develop; visualize with H$_2$SO$_4$ ($R_f$ product=0.5). Remove solvent by rotary evaporation using high vacuum. Partition between 250 ml EtOAc and 100 ml H$_2$O. Wash $3\times 130$ ml brine. Combine aqueous layers and extract with 300 ml EtOAc. Dry the organics over anhydrous Na$_2$SO$_4$. Remove solvent by rotary evaporation in vacuo. Co-evaporate $2\times 50$ ml anhydrous pyridine. Immediately add 41 ml anhydrous dioxane. Swirl flask to achieve complete solution. Add 7.5 ml anhydrous pyridine and p-nitrophenol (2.15 g, 15.5 mmol) to flask with magnetic stirring. Cool reaction flask to 25° C. Add dicyclohexylcarbodiimide (2.92 g, 14.3 mmol, MW 204.35) with stirring, and stir at room temperature for 4 hours. Add 1.6 ml triethylamine and stir 10 minutes. Filter reaction mixture through a sintered glass funnel directly into 18 g long chain alkylamine CPG. Agitate the CPG mixture for 24 hours. Collect the derivatized CPG by filtration into a clean 600 ml sintered glass funnel. Wash with $3\times 500$ ml DMF, $3\times 500$ ml MeOH, and $3\times 500$ ml ether. Transfer the CPG to a clean, dry 500 ml RB flask and dry on the rotovap, using aspirator, then pump at hard vacuum for an hour to remove all solvents. Mix together 12.7 ml acetic anhydride, 51 ml anhydrous pyridine, and 236 mg DMAP. Cap the CPG by adding this solution to the dry CPG and swirl on orbital shaker for 2 hours. Collect the capped CPG by filtration in a clean 500 ml sintered glass funnel. Wash with $1\times 1000$ ml pyridine, $3\times 500$ ml DMF, $2\times 500$ ml water, $3\times 500$ ml MeOH, and $3\times 500$ ml ether. Dry in vacuo. Yield: 18 g.

EXAMPLE 17

Preparation of Acridine-ON™ CPG (Compound 17/Structure X).

Dissolve 1-O-DMT-2-(N-acridine-4-aminobutyryl)-1,3-propanediol (7.2 g, 10.4 mmol) (7) in 30 ml anhydrous pyridine with stirring. Stir at room temperature. Add p-dimethylamino-pyridine (0.584 g, 4.8 mmol) and succinic anhydride (0.863 g, 8.63 mmol). Stir reaction mixture at room temperature for 24 hours. Analyze by TLC to check whether reaction is completed, using 1:1 MeOH:CH$_2$Cl$_2$ with 4 drops of NH$_4$OH added to develop; visualize with H$_2$SO$_4$ ($R_f$ product=0.5). Remove solvent by rotary evaporation using high vacuum. Partition between 250 ml EtOAc and 100 ml H$_2$O. Wash $3\times 130$ ml brine. Combine aqueous layers and extract with 300 ml EtOAc. Dry the organics over anhydrous Na$_2$SO$_4$. Remove solvent by rotary evaporation in vacuo. Co-evaporate $2\times 50$ ml anhydrous pyridine. Immediately add 41 ml anhydrous dioxane. Swirl flask to achieve complete solution. Add 7.5 ml anhydrous pyridine and p-nitrophenol (2.15 g, 15.5 mmol) to flask with magnetic stirring. Cool reaction flask to 25° C. Add dicyclohexylcarbodiimide (2.92 g, 14.3 mmol, MW 204.35) with stirring, and stir at room temperature for 4 hours. Add 1.6 ml triethylamine and stir 10 minutes. Filter reaction mixture through a sintered glass funnel directly into 18 g long chain alkylamine CPG. Agitate the CPG mixture for 24 hours. Collect the derivatized CPG by filtration into a clean 600 ml sintered glass funnel. Wash with $3\times 500$ ml DMF, $3\times 500$ ml MeOH, and $3\times 500$ ml ether. Transfer the CPG to a clean, dry 500 ml RB flask and dry on the rotovap, using aspirator, then pump at hard vacuum for an hour to remove all solvents. Mix together 12.7 ml acetic anhydride, 51 ml anhydrous pyridine, and 236 mg DMAP. Cap the CPG by adding this solution to the dry CPG and swirl on orbital shaker for 2 hours. Collect the capped CPG by filtration in a clean 500 ml sintered glass funnel. Wash with 1×1000 ml pyridine, 3×500 ml DMF, 2×500 ml water, 3×500 ml MeOH, and 3×500 ml ether. Dry in vacuo. Yield: 18 g.

EXAMPLE 18

General Procedure: Preparation of Modified Oligonucleotides Using Phosphoramidite Reagents, Compounds 8-12

Modified oligonucleotides were synthesized on a 1.0 μmol scale using a Milligen/Biosearch 8750 DNA Synthesizer with standard manufacturer procedures for cyanoethyl phosphoramidite chemistry. The modified reagents (8-12) were used in a concentration of 0.1M without any increased coupling times. After synthesis of modified oligonucleotides, cleavage from CPG support and deprotection were performed by treatment with concentrated ammonium hydroxide at 55° C. for 6 hours. In the case of oligonucleotides modified with Acridine-ON TM Phosphoramidite (13), cleavage and deprotection were performed by treatment with 0.4M NaOH in methanol:water (4:1) for 16 hours at room temperature, followed by pH neutralization to pH 9.0 with 2M TEAB, and desalting on a Sephadex G-25 column. HPLC purification was performed employing an Analtech RP-C18 column (1×25 cm); Solvent A=0.1M TEAA pH 7; Solvent B=50% acetonitrile in Solvent A, 30–75% B, 60 minutes, 0.75 ml/minute, 260 nm. Modified oligonucleotides were analyzed by both polyacrylamide electrophoresis (20% denaturing) and analytical HPLC (RP-C18, 0.46×15 cm, 15%–70% B, 30 minutes, 0.75 ml/minute, 260 nm).

EXAMPLE 19

General Procedure: Preparation of 3' Modified Oligonucleotides Using CPG Reagents Compounds 13-17

3' modified oligonucleotides were synthesized on a 1.0 μmol scale using a Milligen/Biosearch 8750 DNA Synthesizer with standard manufacturer procedures for cyanoethyl phosphoramidite chemistry. The modified reagents (13-17) were packed in standard columns and installed in the DNA synthesizer in the same fashion as normal CPG columns are used. After synthesis of modified oligonucleotides, cleavage from CPG support and deprotection were performed by treatment with concentrated ammonium hydroxide at 55° C. for 6 hours. In the case of oligonucleotides modified with Acridine-ON TM CPG (18), cleavage and deprotection were performed by treatment with 0.4M NaOH in methanol:water (4:1) for 16 hours at room temperature, followed by pH neutralization to pH 9.0 with 2M TEAB, and desalting on a Sephadex G-25 column. HPLC purification was performed employing an Analtech RP-C18 column (1×25 cm); Solvent A=0.1M TEAA, pH 7; Solvent B=50% acetonitrile in Solvent A, 30–75% B, 60 minutes, 0.75 ml/minute, 260 nm. Modified oligonucleotides were analyzed by both polyacrylamide electrophoresis (20% denaturing) and analytical HPLC (RP-C18, 0.46×15 cm, 15%–70% B, 30 minutes, 0.75 ml/minute, 260 nm).

EXAMPLE 20

Protocol for Use of 3' Biotin-ON TM CPG With Automated DNA Synthesizer

Attach a 3' Biotin-ON TM CPG to the automated DNA synthesizer. Enter the desired oligonucleotide sequence for synthesis. Make sure the 3' terminal base of the entered sequence is entered as the second base from the 3' end. Note that 3' Biotin-ON TM CPG has a multifunctional linking arm attached to it instead of a 3' terminal nucleotide. Hence, the 3' base is not on the CPG as with normal oligonucleotide synthesis. This must be accounted for when the sequence is entered. Because automated synthesizers assume that the 3' nucleotide is pre-attached to the CPG, a nonsense base must be entered at the 3' terminus when using 3' Biotin-ON TM CPG.

Initiate the synthesis using the TRITYL-ON mode. It is recommended that the trityl group be left on when using Clontech's Oligonucleotide Purification/Elution Cartridge (OPEC) Columns (Cat. #K1077-1, Clontech, Palo Alto, Calif.) for easy purification. However, if other purification methods are employed, the TRITYL-OFF mode may be more desirable.

The extent of 3' biotin incorporation should be determined by measuring the deprotected DMT cation concentration of the first coupling step at 497 nm.

EXAMPLE 21

Protocol for Use of Biotin-ON TM Phosphoramidite and LC-Biotin-ON TM Phosphoramidite with Automated DNA Synthesizers Dissolve the reagent in anhydrous acetonitrile according to the following table to give a concentration of 0.1M.

TABLE 1

| Biotin-ON TM Phosphoramidite | | LC-Biotin-ON TM Phosphoramidite | |
|---|---|---|---|
| Amount | Dilution Volume | Amount | Dilution Volume |
| 50 mg | 0.6 ml | 50 mg | 0.5 ml |
| 100 mg | 1.15 ml | 100 mg | 1.0 ml |
| 250 mg | 2.9 ml | 250 mg | 2.5 ml |

Transfer the solution to the extra phosphoramidite port on the DNA synthesizer (the reagents are supplied in an ABI industrial standard vial). It is recommended to make all transfers of anhydrous acetonitrile with a syringe for ease of handling and for minimum exposure to air. The reagents should be used immediately after dissolving.

Enter in the oligonucleotide sequence to be synthesized. The reagents can be programmed to couple at any nucleotide position in the oligonucleotide sequence. Multiple reagent units can be added by programming multiple coupling cycles. Separation of reagent sites by at least one normal nucleotide is beneficial for subsequent streptavidin binding.

Carefully prime the reagent line on the DNA synthesizer. The line must be well primed to obtain optimum coupling efficiency.

Initiate the synthesis using the TRITYL-ON mode. It is recommended that the trityl group be left on when using Clontech's OPEC Columns for easy purification. However, if other purification methods are employed, the TRITYL-OFF mode may be more desirable. Note: if the DNA synthesizer used has programming capabilities, it is recommended that a longer coupling time be programmed for these reagents (up to 5-10 minutes). This will ensure high coupling efficiency.

To monitor the incorporation of the reagents, measure the dimethoxytrityl cation concentration at 497 nm. If the reagent is being incorporated at the 5' terminus of the oligonucleotide, the TRITYL-OFF mode must be used. If the reagent is to incorporated at the 5' terminus and OPEC columns are used for purification, then the TRITYL-ON mode must be used, and therefore coupling efficiency cannot be measured.

EXAMPLE 22

Protocol for Manual Biotinylation of Biotin-ON ™ Phosphoramidite and LC-Biotin-ON ™ Phosphoramidite Reagents A convenient manual procedure can be employed to conserve the reagents. This procedure uses only 50 mg of reagent.

Synthesize the oligonucleotide on the DNA synthesizer according to standard procedures. Program the DNA synthesizer to pause just before the reagent coupling step. Pause the DNA synthesizer immediately after the deblocking step. This can be manually performed if necessary. Make sure the deblocking solution has been thoroughly rinsed out of the column before pausing the synthesis.

Dissolve 50 mg of reagent in 0.5 ml anhydrous acetonitrile and 0.5 ml activator (saturated tetrazole in anhydrous acetonitrile). This should be performed with a 1.0 ml syringe and needle. Remove the CPG column from the synthesizer and react with reagent/activator solution using two 1.0 ml luer tip syringes. Periodically swish the solution back and forth with plungers for 5 minutes. Install the CPG column back into the DNA synthesizer and restart the synthesis. Make sure to restart the coupling step and restart at the oxidation step.

Alternatively, the reagent coupling cycle can be completed manually on the DNA synthesizer with the following steps:

| Acetonitrile wash (2x) | 15 seconds (each) |
|---|---|
| Oxidation | 15 seconds |
| Acetonitrile wash (2x) | 15 seconds (each) |
| Capping | 15 seconds |
| Acetonitrile wash (2x) | 15 seconds (each) |

The final deblocking step is optional depending on how the biotinylated oligonucleotide is purified. If using the OPEC columns, the trityl group must be left on.

EXAMPLE 23

Deprotection and Cleavage

Cleave the biotinylated oligonucleotide from the solid support by treating it with 1 ml of ammonium hydroxide at room temperature for 1.5–2.0 hours. It is convenient to use luer tip syringes for this step. Care should be taken not to let the ammonia evaporate. Complete the deprotection by transferring the ammonium hydroxide to a 1.5 ml screw cap microcentrifuge tube and heat at 55° C. for 6 hours (the incorporated biotin moiety is stable to ammonium hydroxide at 55° C.). Caution: ammonia gas builds up pressure at 55° C. in a closed reaction vessel; cool to 4° C. before opening screw cap microcentrifuge tube.

If OPEC columns are to be used for purification, do not evaporate off the ammonium hydroxide solution, but proceed directly to the procedure outlined in Example 24, below. If OPEN columns are not to be used for purification, evaporate to dryness by vacuum centrifugation or rotary evaporation. The biotinylated oligonucleotide is now ready for purification using conventional methods such as reverse phase HPLC, anion exchange HPLC, and polyacrylamide gel electrophoresis.

EXAMPLE 24

Purification of Biotinylated Oligonucleotides with OPEC Columns

In many applications, further purification may not be necessary. However, to achieve optimum results, purification of biotinylated oligonucleotides with OPEC columns is recommended. Purified oligonucleotides can be obtained in less than 30 minutes. When using OPEC columns, it is necessary to leave the trityl group on the oligonucleotide, i.e., a TRITYL-ON synthesis must be performed.

The procedure is as follows: connect a syringe to the female luer end of the OPEC column. Direct the male end of the column to a waste vessel. Fill the syringe with 2 ml of HPLC grade acetonitrile and gently push it through the column at a rate of approximately 1–2 drops per second. All subsequent steps should also be carried out a flow rate of 1–2 drops per second. Wash the OPEC column with 2 ml of 2.0M TEAA. Add 0.5 ml deionized water to the cleaved, deprotected oligonucleotide in the ammonium hydroxide solution. Slowly load this solution onto the column. Collect the eluent into a clean tube. Recycle the eluent collected through the OPEC column, again collecting the eluent into a fresh tube. The final eluent may be retained and purified further on other columns until all trityl oligonucleotide is exhausted. When used according to this protocol, up to 25 OD units of oligonucleotide can be purified.

Wash the column with 3 ml of ammonium hydroxide/water (1:10, w/v). Wash the column with 2 ml deionized water. Detritylate the support-bound oligonucleotide by treating the column with 2 ml of 2% TFA at a rate of 1–2 drops per second. Proceed immediately to the next step, as prolonged exposure to TFA will result in decomposition of the oligonucleotide. Wash the OPEC column with 5 ml deionized water. Elute the purified, detritylated oligonucleotide with 20% acetonitrile. Collect eluted fractions of 4 drops each. The first 4 drops of eluent can be discarded. The product is normally in the following 4–10 drops. To determine the OD units at 260 nm, evaporate an aliquot of the elute and redissolve it in water. Store unused oligonucleotide at −20° C.

EXAMPLE 25

Confirmation of Biotin Label

The presence of biotin can be determined by a p-dimethylaminocinnamaldehyde colorimetric test. Spot 0.2 OD of biotinylated oligonucleotide on a silica gel TLC plate. Dry plate thoroughly. Spray with a solution of 2% p-dimethylaminocinnamaldehyde, 2% sulfuric acid in ethanol. Heat plate with gentle warming. The presence of biotin is indicated by a pink-red spot. It is recommended to run a negative control as reference.

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A reagent for use in oligonucleotide synthesis having the following structure:

wherein n is from 0 to about 15;

R₁ is selected from the group consisting of dimethoxytrityl (DMT) and monomethoxytrityl;

R₂ is selected from the group consisting of controlled pore glass (CPE); alkylamine controlled pore glass, wherein alkyl is 1 to 50 carbon atoms; polystyrene; divinylbenzene;

and salts thereof, wherein R₅ and R₆ are independently selected from the group consisting of $C_{3-10}$ branched alkyl, $C_{1-12}$ unbranched alkyl, and cyclic hydrocarbons; and Y is a beta-cyanoethyl group;

X₁ is a functional group selected from the group consisting of oxygen, sulfur, or —NH;

R₃ is a reporter molecule or protecting group selected from the group consisting of biotin, rhodamine, Fmoc, fluorescein, dinitrophenyl, cholesterol, and acridine.

2. The reagent, according to claim 1, wherein R₂ is selected from the group consisting of and salts thereof, wherein R₅ and R₆ are independently selected from the group consisting of $C_{3-10}$ branched alkyl and $C_{1-12}$ unbranched alkyl and cyclic hydrocarbons, and Y is a beta-cyanoethyl group.

3. The reagent, according to claim 1, wherein R₂ is CPG or alkylamine CPG, wherein alkyl is 1 to 50 carbon atoms.

4. The reagent, according to claim 1, wherein R₂ is polystyrene or divinylbenzene.

5. The reagent for use in oligonucleotide synthesis, according to claim 1, having the following structure:

6. A reagent for use in oligonucleotide synthesis having the following structure:

7. The reagent for use in oligonucleotide synthesis, according to claim 1, having the following structure:

8. The reagent for use in oligonucleotide synthesis, according to claim 1, having the following structure:

9. The reagent for use in oligonucleotide synthesis, according to claim 1, having the following structure:

10. The reagent, according to claim 1, having the structure:

11. The reagent, according to claim 1, having the structure:

12. The reagent, according to claim 1, having the structure:

13. The reagent, according to claim 1, having the structure:

14. The reagent, according to claim 1, having the structure:

15. The reagent for use in oligonucleotide synthesis, according to claim 1, having the following structure:

\* \* \* \* \*

UNITED STATES PATENT AND TRADEMARK OFFICE
CERTIFICATE OF CORRECTION

PATENT NO. : 5,451,463
DATED : September 19, 1995
INVENTOR(S) : Paul S. Nelson, Mark A. Kent It is certified that error appears in the above-indentified patent and that said Letters Patent is hereby corrected as shown below:

Column 2: line 29: "Nucl. Acids Res. 5305-5321)" should read --Nucl. Acids Res. 15:5305-5321)--.

Column 3: line 11: "$R_5=R_6 32\ CH(CH_3)_2$." should read --$R_5=R_6=CH(CH_3)_2$.--; line 16: "divinylbenze." should read --divinylbenzene.--.

Column 12: line 6: "-1.3-propanediol" should read ---1,3-propanediol--.

Column 15: line 30: "0.1M TEAA pH7;" should read --0.1 M TEAA, pH 7;--.

Signed and Sealed this

Ninth Day of January, 1996

Attest:

BRUCE LEHMAN

*Attesting Officer*          *Commissioner of Patents and Trademarks*